(12) United States Patent
Okada et al.

(10) Patent No.: US 8,251,213 B2
(45) Date of Patent: Aug. 28, 2012

(54) PATCH PACKAGE STRUCTURE

(75) Inventors: Katsuhiro Okada, Ibaraki (JP);
Yoshihiro Iwao, Ibaraki (JP); Kensuke Matsuoka, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 750 days.

(21) Appl. No.: 12/167,085

(22) Filed: Jul. 2, 2008

(65) Prior Publication Data
US 2009/0011159 A1    Jan. 8, 2009

(30) Foreign Application Priority Data

Jul. 4, 2007 (JP) ................................. 2007-175809

(51) Int. Cl.
*A61B 17/06* (2006.01)
(52) U.S. Cl. .................. 206/441; 206/440; 206/484
(58) Field of Classification Search .............. 206/440, 206/441, 460, 484, 447, 582; 424/448, 449; 604/307, 308, 289, 304
See application file for complete search history.

(56) References Cited

U.S. PATENT DOCUMENTS

| | | | |
|---|---|---|---|
| 3,612,265 A | | 10/1971 | Dickerson |
| 4,687,476 A | * | 8/1987 | Pailin .............................. 604/307 |
| 5,505,306 A | | 4/1996 | Akemi et al. |
| 5,950,830 A | * | 9/1999 | Trigger .......................... 206/440 |
| 6,120,792 A | * | 9/2000 | Juni ............................... 424/448 |
| 6,617,486 B1 | * | 9/2003 | Murata ............................ 602/48 |
| 6,622,865 B1 | | 9/2003 | Theobald |
| 6,787,681 B2 | * | 9/2004 | Murakami et al. ............... 602/57 |
| 6,855,861 B2 | * | 2/2005 | Dotta .............................. 602/57 |
| 2003/0138479 A1 | * | 7/2003 | Mizota et al. .................. 424/443 |
| 2006/0000734 A1 | | 1/2006 | Ninomiya et al. |
| 2007/0144928 A1 | * | 6/2007 | Higo et al. ..................... 206/438 |

(Continued)

FOREIGN PATENT DOCUMENTS

JP          07-080040          3/1995

(Continued)

OTHER PUBLICATIONS

Chinese Office Action issued on Nov. 10, 2010 in the corresponding Chinese Patent Application No. 200810128308.9.

(Continued)

*Primary Examiner* — David Fidei
(74) *Attorney, Agent, or Firm* — Sughrue Mion, PLLC

(57) ABSTRACT

The present invention relates to a patch package structure which includes: a package including a first sheet material and a second sheet material, the first and second sheet materials being sealed together in peripheral parts thereof; and a patch disposed in the package, the patch contains a backing, a pressure-sensitive adhesive layer laminated on at least one side of the backing, and a release liner which protects a pressure-sensitive adhesive surface of the pressure-sensitive adhesive layer, the release liner having on a surface thereof a cut line supporting a peel-off of the release liner at the time of using the patch, the patch being disposed in the package so that the release liner faces the inner surface of the first sheet material, the first sheet material having a first region in which the inner surface of the first sheet material faces the cut line of the release liner, the first sheet material having in the first region a minimum first distance between the inner surface of the first sheet material and the surface of the release liner, and the inner surface of the first sheet material being spaced from the surface of the release liner at the minimum first distance in the first region.

7 Claims, 10 Drawing Sheets

U.S. PATENT DOCUMENTS

| | | |
|---|---|---|
| 2008/0172015 A1 | 7/2008 | Okada et al. |
| 2009/0194447 A1* | 8/2009 | Okada et al. .................. 206/440 |
| 2010/0122927 A1* | 5/2010 | Matsuoka et al. ............ 206/438 |
| 2010/0158991 A1* | 6/2010 | Okada et al. .................. 424/448 |

FOREIGN PATENT DOCUMENTS

| | | |
|---|---|---|
| JP | 10-310108 | 11/1998 |
| JP | 10-511330 A | 11/1998 |
| JP | 2002-535209 A | 10/2002 |
| JP | 2008-188414 A | 8/2008 |
| KR | 1020060049771 A | 5/2006 |
| WO | 00/69422 A1 | 11/2000 |
| WO | 01/60295 A2 | 8/2001 |
| WO | 2005-048910 A1 | 6/2005 |

OTHER PUBLICATIONS

Extended European Search Report dated Sep. 23, 2008.

Canadian Office Action issued on Nov. 8, 2010 in the corresponding Canadian Patent Application No. 2636570.

Korean Office Action issued on Jul. 20, 2011 in the corresponding Korean Patent Application No. 10-2008-0064618.

English Translation of Japanese Office Action issued in Application No. 2007-175809 dated Jan. 10, 2012.

Communication dated Mar. 31, 2012 from the Korean Intellectual Property Office in counterpart Korean application No. 10-2008-64618.

* cited by examiner

PATCH PACKAGE STRUCTURE

FIELD OF THE INVENTION

The present invention relates to a patch package structure which includes: a package including a first sheet material and a second sheet material, the first and second sheet materials being sealed together in peripheral parts thereof; and a patch disposed in the package.

BACKGROUND OF THE INVENTION

Patches to be applied to the skin for the purpose of, e.g., protecting the affected part and adhesive preparations to be applied to a surface of the skin of a mammal for the purpose of percutaneously administering a drug to the mammal have hitherto been developed.

Such a patch generally includes a backing, a pressure-sensitive adhesive layer laminated on at least one side of the backing, and a release liner which protects the pressure-sensitive adhesive surface of the pressure-sensitive adhesive layer. When such a patch is used, the release liner is peeled off and removed. In some patches, the release liner has a cut line in a surface thereof so as to facilitate the peeling of the release liner. The user utilizes the cut line for securing a hold for peeling off the release liner by pinching the cut areas with fingers to peel off the release liner.

WO 00/69422 pamphlet describes a patch having a release liner in which the release liner can be made easily peelable by forming a cut line of a given shape on a surface of the release liner. However, this patch has such a drawback that components of the pressure-sensitive adhesive layer may protrude from or flow out through the cut line and adhere to inner surfaces of the package in which the patch is placed, whereby it might become difficult to take the patch out of the package or the components of the pressure-sensitive adhesive layer may adhere to the hand of the user to give an uncomfortable feeling.

Techniques for avoiding the adhesion of components of the pressure-sensitive adhesive layer to the inner surface of the package include, for example, the following technique. JP-T-10-511330 (the term "JP-T" as used herein means a published Japanese translation of a PCT patent application) discloses a patch package structure in which a patch 1 having a release liner 3 is placed in a blister pack 12 and sealed with a sheet material 14. This patch package structure is shown in FIG. 10. The release liner 3 of the patch 1 has, formed on a surface thereof, a cut line 9 supporting the peel-off of the release liner. It is disclosed that this patch package structure has a given shape so that, even if components of the pressure-sensitive adhesive layer protrude from an edge of the patch 1, the components are less apt to adhere to the inner surfaces of the package.

However, since the cut line 9 of the patch can freely come into contact with the sheet material 14 in this package structure, there is a fear that, when components of the pressure-sensitive adhesive layer protrude from the cut line 9, then the components may adhere to an inner surface of the package to make it difficult to take out the patch or may adhere to the hand of the user to give an uncomfortable feeling.

Furthermore, in these documents, no statement can be found concerning the necessity of inhibiting components of the pressure-sensitive adhesive layer which have protruded from or flowed out through the cut line on a surface of the release liner from adhering to an inner surface of the package.

Recently, soft pressure-sensitive adhesive layers such as those holding a large amount of a liquid component therein tend to be employed for the purpose of improving a soft wear feeling during wear of the patch or the purpose of reducing the skin irritation caused by separation of the horny layer upon stripping of the patch. Further, with regard to adhesive preparations in which the pressure-sensitive adhesive layer contains a drug, a pressure-sensitive adhesive layer having a larger thickness has been frequently employed in recent adhesive preparations so that the pressure-sensitive adhesive layer can hold a large amount of a drug. As described above, in such cases where the pressure-sensitive adhesive layer contains a large amount of a liquid component or the pressure-sensitive adhesive layer is thick, the problem described above is apt to be actualized. Consequently, there has been a strong desire for a patch package structure in which a patch can be easily taken out of the package and can be comfortably used.

SUMMARY OF THE INVENTION

In view of the above, an object of the invention is to inhibit components of the pressure-sensitive adhesive layer which have protruded from or flowed out through a cut line formed on a surface of the release liner of a patch from adhering to an inner surface of the package.

The present inventors have made intensive studies. As a result, it has been found that, by molding a sheet material facing a cut line of a release liner of a patch into a given shape, even if components of the pressure-sensitive adhesive layer protrude from or flow out through the cut line, the components of the pressure-sensitive adhesive layer can be inhibited from adhering to the sheet material, whereby the patch can be easily taken out of the package. The inventors have further found a new effect that, in this package structure, load imposition on the vicinity of the cut line of the patch is avoided and the protrusion or outflow of components of the pressure-sensitive adhesive layer is also inhibited unexpectedly. The invention has been thus completed based on these findings. Accordingly, the invention provides the following (1) to (8).

According to an embodiment, there is provided a patch package structure which comprises:

a package comprising a first sheet material and a second sheet material, said first and second sheet materials being sealed together in peripheral parts thereof; and a patch disposed in the package, wherein the patch comprises a backing, a pressure-sensitive adhesive layer laminated on at least one side of the backing, and a release liner which protects a pressure-sensitive adhesive surface of the pressure-sensitive adhesive layer, said release liner having on a surface thereof a cut line supporting a peel-off of the release liner at the time of using the patch, wherein the patch is disposed in the package so that the release liner faces the inner surface of the first sheet material, and wherein the first sheet material has a first region in which the inner surface of the first sheet material faces the cut line of the release liner, and the first sheet material has in the first region a minimum first distance between the inner surface of the first sheet material and the surface of the release liner, said inner surface of the first sheet material being spaced from the surface of the release liner at the minimum first distance in the first region.

According to an embodiment, the first sheet material has in the first region a protrudent part which projects toward the outside of the package, said protrudent part having a planar outer shape which includes a planar outer shape of the cut line.

According to an embodiment, the first sheet material has a second region in which the inner surface of the first sheet material does not face the cut line of the release liner, and the first sheet material has in the second region a recessed part which is depressed toward the inside of the package.

According to an embodiment, the second sheet material has a protrudent part which protrudes toward the outside of the package, said protrudent part having a planar outer shape which includes a planar outer shape of the patch.

According to an embodiment, the protrudent part of the second sheet material has a side part and an upper part, and the upper part has a recessed part which is depressed toward the inside of the package, said recessed part being disposed at such a position that the inner surface of the package at the recessed part does not come into contact with a part of the backing which corresponds to the cut line of the release liner of the patch.

According to an embodiment, the protrudent part of the second sheet material has a side part and an upper part, and the side part has a depressed part which is depressed toward the inside of the package, said patch being supported by the inner surface of the second sheet material at the depressed part.

According to an embodiment, the pressure-sensitive adhesive layer of the patch contains a liquid component.

According to an embodiment, the patch is an adhesive preparation comprising a pressure-sensitive adhesive layer containing a drug.

In the patch package structure of the invention, the patch is disposed in the package so that the release liner faces the inner surface of the first sheet material. The first sheet material has a first region in which the inner surface of the first sheet material faces the cut line of the release liner. In the first region, the inner surface of the first sheet material and the surface of the release liner of the patch disposed in the package provide a minimum first distance between them. Since the inner surface of the first sheet material and the cut line formed on a surface of the release liner are spaced from each other at the minimum first distance, they are less apt to come into contact with each other. Accordingly, even if components of the pressure-sensitive adhesive layer protrude from or flow out through the cut line, the components of the pressure-sensitive adhesive layer are less apt to adhere to the inner surface of the package containing the patch. Consequently, the patch can be easily taken out of the package.

Furthermore, unexpectedly, since the inner surface of the first sheet material in the patch package structure of the invention is less apt to come into contact with the cut line on a surface of the release liner, a part of the patch which is near to the cut line are less apt to receive a load from outside the package structure through the package. Consequently, the patch package structure attains a new effect that the protrusion or outflow of the components of the pressure-sensitive adhesive layer from the cut line is inhibited. As a result, the possibility that the components of the pressure-sensitive adhesive layer might adhere to the hand of the user at the time of use to give an uncomfortable feeling is significantly diminished.

Accordingly, the patch package structure of the invention therefore has advantages that the components of the pressure-sensitive adhesive layer are less apt to protrude from or flow out through the cut line on a surface of the release liner and that the user is less apt to feel uncomfortable, e.g., to come to have a sticky hand. Further, even if components of the pressure-sensitive adhesive layer protrude or flow out, the components of the pressure-sensitive adhesive layer are less apt to adhere to the inner surface of the package and the patch can be easily taken out of the package. Therefore, according to the patch package structure of the invention, the patch can be used extremely comfortably.

Figure 1:
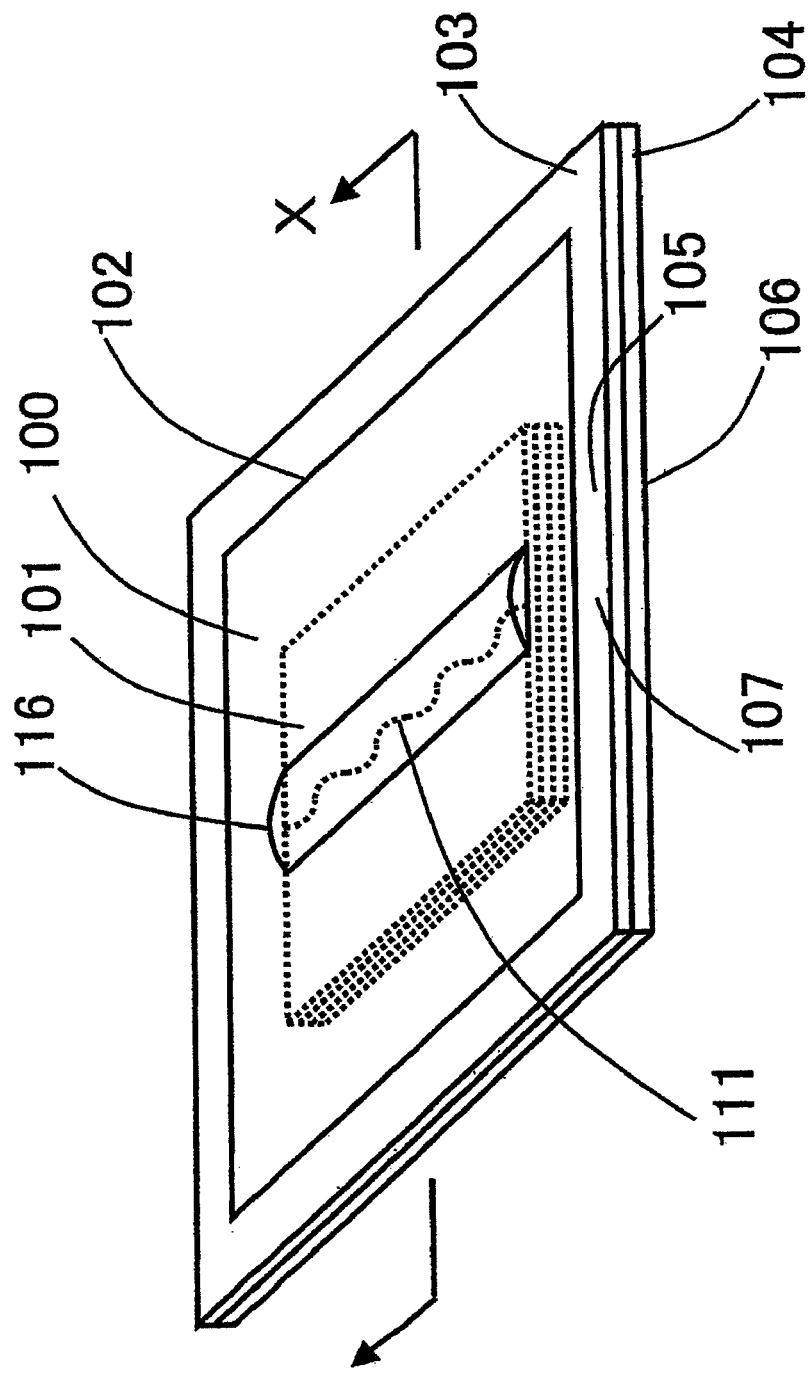
FIG. 1 is a slant view of one embodiment of the patch package structure of the invention.

DESCRIPTION OF THE REFERENCE NUMERALS AND SIGNS 100 patch package structure
101 patch
102 package
103 first sheet material
104 second sheet material
105 peripheral part of first sheet material
106 peripheral part of second sheet material
107 sealed part
111 cut line
116 protrudent part
200 patch package structure
201 patch
202 package
203 first sheet material
204 second sheet material
205 peripheral part of first sheet material
206 peripheral part of second sheet material
208 backing
209 pressure-sensitive adhesive layer
210 release liner
211 cut line
212 first region
213 second region
214 minimum first distance
215 distance between inner surface of first sheet material and inner surface of second sheet material
216 protrudent part
301 patch
308 backing
309 pressure-sensitive adhesive layer
310 release liner
311 cut line
400 patch package structure
401 patch
402 package
403 first sheet material
411 cut line
417 recessed part 501 patch
502 package
503 first sheet material
504 second sheet material
509 pressure-sensitive adhesive layer
510 release liner
511 cut line
512 first region
513 second region
514 minimum first distance
517 recessed part
600 patch package structure
601 patch
602 package
603 first sheet material
604 second sheet material
609 pressure-sensitive adhesive layer
610 release liner
611 cut line
612 first region
613 second region
616 protrudent part
618 height
619 protrudent part
700 patch package structure
701 patch
702 package
703 first sheet material
704 second sheet material
709 pressure-sensitive adhesive layer
711 cut line
712 first region
713 second region
719 protrudent part
720 recessed part
721 part of backing corresponding to cut line
800 patch package structure
801 patch
802 package
803 first sheet material
804 second sheet material
810 release liner
811 cut line
812 first region
813 second region
816 protrudent part
819 protrudent part
820 recessed part
900 patch package structure
901 patch
902 package
903 first sheet material
904 second sheet material
909 pressure-sensitive adhesive layer
910 release liner
911 cut line
912 first region
914 minimum first distance
919 protrudent part
922 depressed part

DETAILED DESCRIPTION OF THE INVENTION

Preferred embodiments of the invention are shown below. However, the following detailed explanations thereon and specific embodiments are intended only for exemplification and should not limit the scope of the invention. The following explanations on preferred embodiments are merely illustrative and are never intended to limit the invention and the applications or uses thereof. Incidentally, each drawing is enlarged in the direction perpendicular to the sheet materials (top-and-bottom direction in the drawing) for the purpose of an easy explanation of the concept of the invention and actual products may be produced in a flatter form.

FIG. 1 is a slant view of an embodiment of the patch package structure of the invention. This patch package structure 100 includes a package 102 and a patch 101 disposed therein. The package 102 is constituted of a first sheet material 103 which is approximately planar and is molded into a given shape and a second sheet material 104 which is approximately planar. The package 102 has a sealed part 107 formed by sealing a peripheral part 105 of the first sheet material 103 and a peripheral part 106 of the second sheet material 104.

Figure 2:
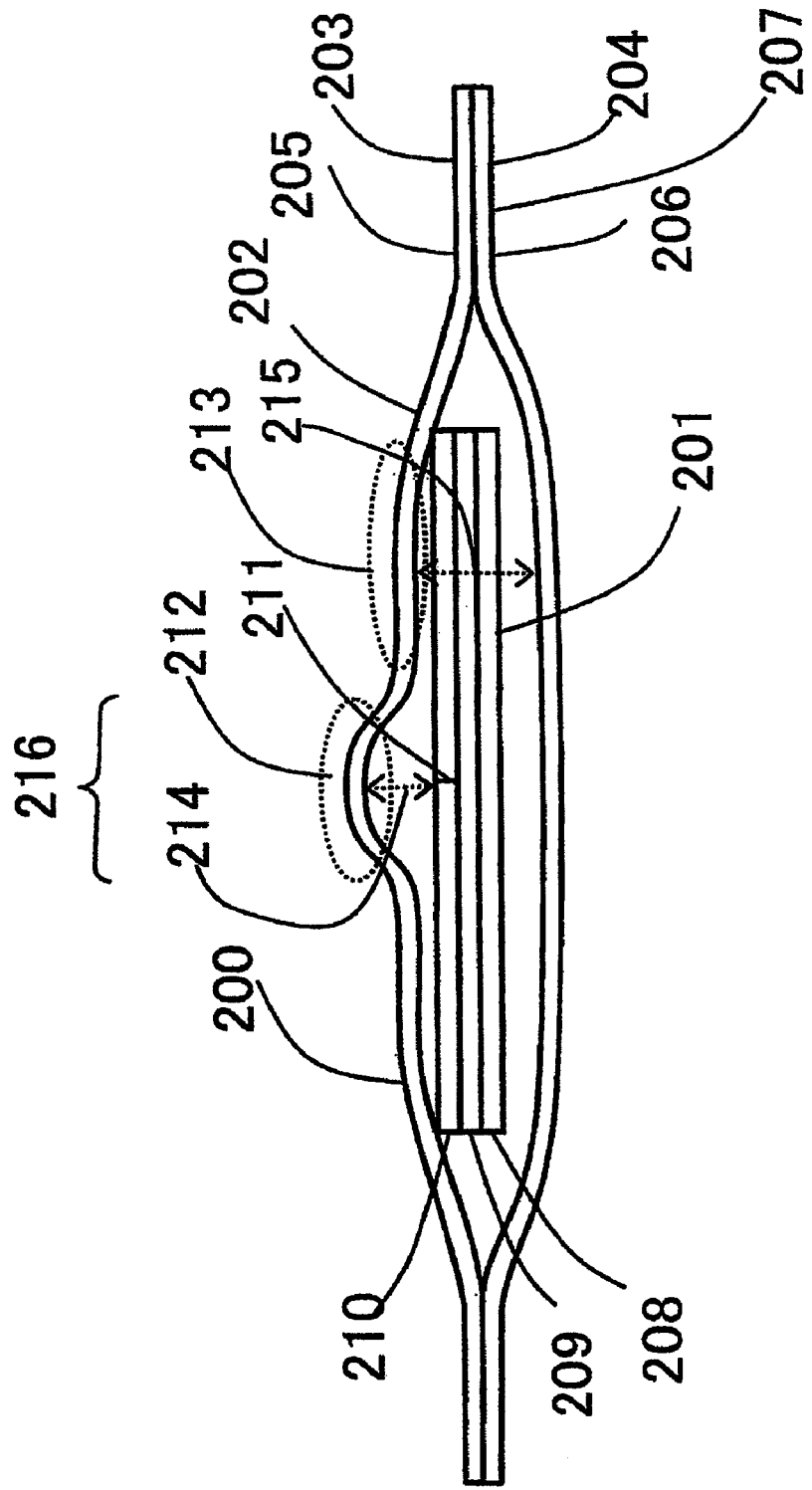
FIG. 2 is a sectional view of the embodiment of the patch package structure of the invention.
Figure 3:
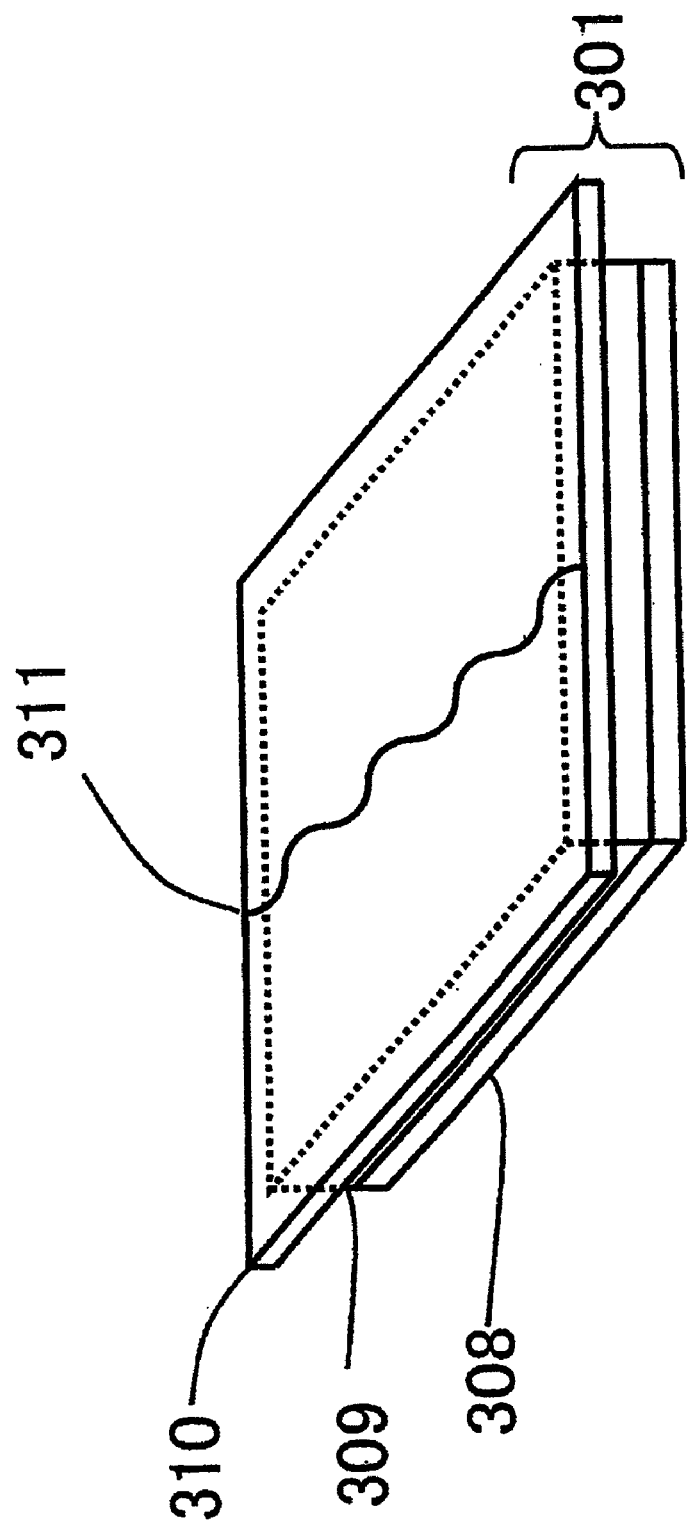
FIG. 3 is a slant view of an embodiment of the patch.

In the next place, with reference to FIG. 2, FIG. 2 is a sectional view diagrammatically illustrating a package section at the position shown by X in FIG. 1. This package structure 200 is constituted of a patch 201 and a package 202. The package 202 has a sealed part 207 formed by sealing a peripheral part 205 of a first sheet material 203 and a peripheral part 206 of a second sheet material 204. The patch 201 is disposed in the package 202 constituted of the first sheet material 203 and second sheet material 204. The package 202 may further contain other contents such as a deoxygenating material according to the necessity. In the patch 201 in this embodiment, the edges of the backing 208, pressure-sensitive adhesive layer 209, and release liner 210 are flush with each other. The patch 201 in this embodiment may be easily produced and hence is low in cost. However, patches such as that which will be described later with reference to FIG. 3 are also preferred.

In the embodiment shown in FIG. 2, the patch 201 is disposed in the package 202 in such a manner that the release liner 210 faces the inner surface of the first sheet material 203. The first sheet material 203 has a first region 212 in which the inner surface of the first sheet material 203 faces the cut line 211 of the release liner 210, and also has a second region 213 in which the inner surface of the first sheet material 203 does not face the cut line 211 of the release liner 210. The first sheet material 203 has been molded, and a protrudent part 216 protruding toward the outside of the package is formed in the first region 212 of the first sheet material 203 so that the first sheet material 203 has in the first region 212 a minimum first distance 214 between the inner surface of the first sheet material 203 and the surface of the release liner 210. The protrudent part 216 has a planar outer shape which includes a planar outer shape of the cut line 211.

The expression "a certain first planar outer shape includes a certain second planar out shape" herein includes the case where a part of the first planar outer shape coincides with a part of the second planar outer shape. In the second region 213, the inner surface of the first sheet material 203 and the inner surface of the second sheet material 204 provide a distance 215 between them.

With reference to FIG. 1 again, the protrudent part 116 has a shape which includes the cut line 111 having a wavy planar shape. The planar outer shape of the protrudent part 116 is not particularly limited so long as the shape thereof includes the planar outer shape of the cut line 111 of the release liner. Examples thereof include substantially quadrangular shapes such as that shown in FIG. 1, substantially polygonal shapes such as substantially rectangular shapes and substantially triangular shapes, substantially elliptic shapes, substantially circular shapes, and other various shapes.

With reference to FIG. 2 again, the minimum first distance 214 described above means the distance provided between the part of the inner surface of the first material 203 which is most apart from the surface of the release liner 210 of the patch 201 and the surface of the release liner 210 of the patch 201, when the patch 201 is located closest to the first sheet material 203. In the first region 212, since the inner surface of the first sheet material 203 and the surface of the release liner 210 of the patch 201 are spaced from each other at the minimum first distance 214, the cut line 211 is less apt to come into contact with the inner surface of the first sheet material 203.

Consequently, even if components of the pressure-sensitive adhesive layer 209 protrude from or flow out through the cut line 211, the components of the pressure-sensitive adhesive layer 209 are effectively inhibited from adhering to the inner surface of the first sheet material 203. Furthermore, since an external load is less apt to be imposed on the patch 201 through the first sheet material 203, the protrusion or outflow of the components of the pressure-sensitive adhesive layer 209 from the cut line 211 is effectively inhibited.

From this standpoint, the minimum first distance 214 is preferably 0.5 mm or longer, more preferably 1.0 mm or longer, most preferably 2.0 mm or longer. On the other hand, in a case where the minimum first distance 214 is too long, there is a possibility that the package structure as a whole becomes thick to thereby result in a decrease in the efficiency of material utilization during the production and in a decrease in the efficiency of storage, transporting, etc. of the patch package structure. From this standpoint, the minimum first distance 214 is preferably 3.0 mm or shorter. Specific examples of the distance between the inner surface of the first sheet material 203 and the inner surface of the second sheet material 204 in the first region include 1.0-4.0 mm. Specific examples of the thickness of the patch 201 include 0.2-0.4 mm.

As stated above, the first sheet material 203 has a second region 213. This second region 213 herein means a region in which the first sheet material 203 does not face the cut line 211 of the release liner 210 but faces the release liner 210. In the second region 213, the distance 215 between the inner surface of the first sheet material 203 and the inner surface of the second sheet material 204 is not particularly limited so long as the distance as measured in a position where the two surfaces are closest to each other is not smaller than the thickness of the patch so as to prevent an unnecessary load from being imposed in the thickness direction on the patch 201. Specific examples of that distance include 0.3-1.0 mm.

In embodiments in which the first sheet material has a protrudent part which protrudes toward the outside of the package, such as that shown in FIGS. 1 and 2, since the volume of the space in the package can be easily reduced, such embodiments are advantageous owing to the high stability of the patch.

In the next place, with reference to FIG. 3, FIG. 3 is a slant view of an embodiment of a patch constituting the patch package structure of the invention. This patch 301 includes a backing 308, a pressure-sensitive adhesive layer 309 laminated on at least one side of the backing, and a release liner 310 which protects the pressure-sensitive adhesive surface of the pressure-sensitive adhesive layer 309. This release liner 310 has, formed on a surface thereof, a cut line 311 supporting the peel-off of the release liner 310 at the time of using the patch.

In the embodiment shown in FIG. 3, the release liner 310 is drawn so as to have a planar outer shape which includes a planar outer shape of the pressure-sensitive adhesive layer 309 and a planar outer shape of the backing 308. In this embodiment, even if components of the pressure-sensitive adhesive layer 309 protrude or flow out from an edge of the patch 301, since the components of the pressure-sensitive adhesive layer 309 are less apt to move to the side of the release liner 310 which is opposite to the pressure-sensitive adhesive layer 309 side, this patch 301, after being disposed in the package, is less apt to adhere to the inner surfaces of the package. This embodiment is therefore preferred.

In the embodiment shown in FIG. 3, the release liner 310 has a wavy cut line 311 formed on a surface thereof so that the user can easily peel off the release liner 310 from the pressure-sensitive adhesive layer 309 at the time of application to the skin. For example, in application of the patch 301, when the user slightly bends the patch 301 so as to form a ridge along the cut line 311, then areas suitable for pinching for peeling off the release liner 310 may be easily obtained. For this reason, such a cut line 311 is formed in the release liner 310.

The planar shape of such a cut line may be a continuous line or a broken line, and the planar shape thereof is not limited to a wavy line and examples thereof include a substantially straight line and a zigzag line. A wavy line or zigzag line is preferred from the standpoint that pinching areas for peeling off the release liner can be of easily obtained. The cut line need not be completely continuous, i.e., may be separated. The cut line may have uncut areas so long as the uncut areas can be broken with fingers or the like.

The plane-direction shape of the patch package structure shown in FIGS. 1 to 3 is not particularly limited. Examples of the planar outer shape of the patch (including the backing, pressure-sensitive adhesive layer, and release liner) and that of the package independently include substantially triangular shapes, substantially quadrangular shapes, substantially polygonal shapes such as substantially rectangular shapes, elliptic shapes, circular shapes, and other various shapes. From the standpoint of the efficiency of utilizing the space in the package in which the patch is disposed, it is preferred that the planar outer shape of the patch and that of the package be similar to each other. From the standpoint of diminishing material discard to effectively utilize materials, the planar outer shape of each of the patch and package preferably is a substantially quadrangular shape such as a substantially rectangular shape. In the case where the edges of the backing, pressure-sensitive adhesive layer, and release liner are flush with each other as in the patch shown in FIGS. 1 and 2, a specific example of the planar outer shape of the patch is a substantially rectangular shape in which one side has a length of 20-100 mm and another side has a length of 20-100 mm. As stated above with regard to FIG. 3, the planar outer shape of the release liner preferably includes both the planar outer shape of the pressure-sensitive adhesive layer and the planar outer shape of the backing. In this case, a specific example of the planar outer shape of the release liner 209 is a substantially rectangular shape in which one side has a length of 22-104 mm and another side has a length of 22-104 mm. The release liner in this case hence has a strip-shaped projecting peripheral area having a width of 1-2 mm which protrudes from the edges of the pressure-sensitive adhesive layer and backing.

Figure 4:
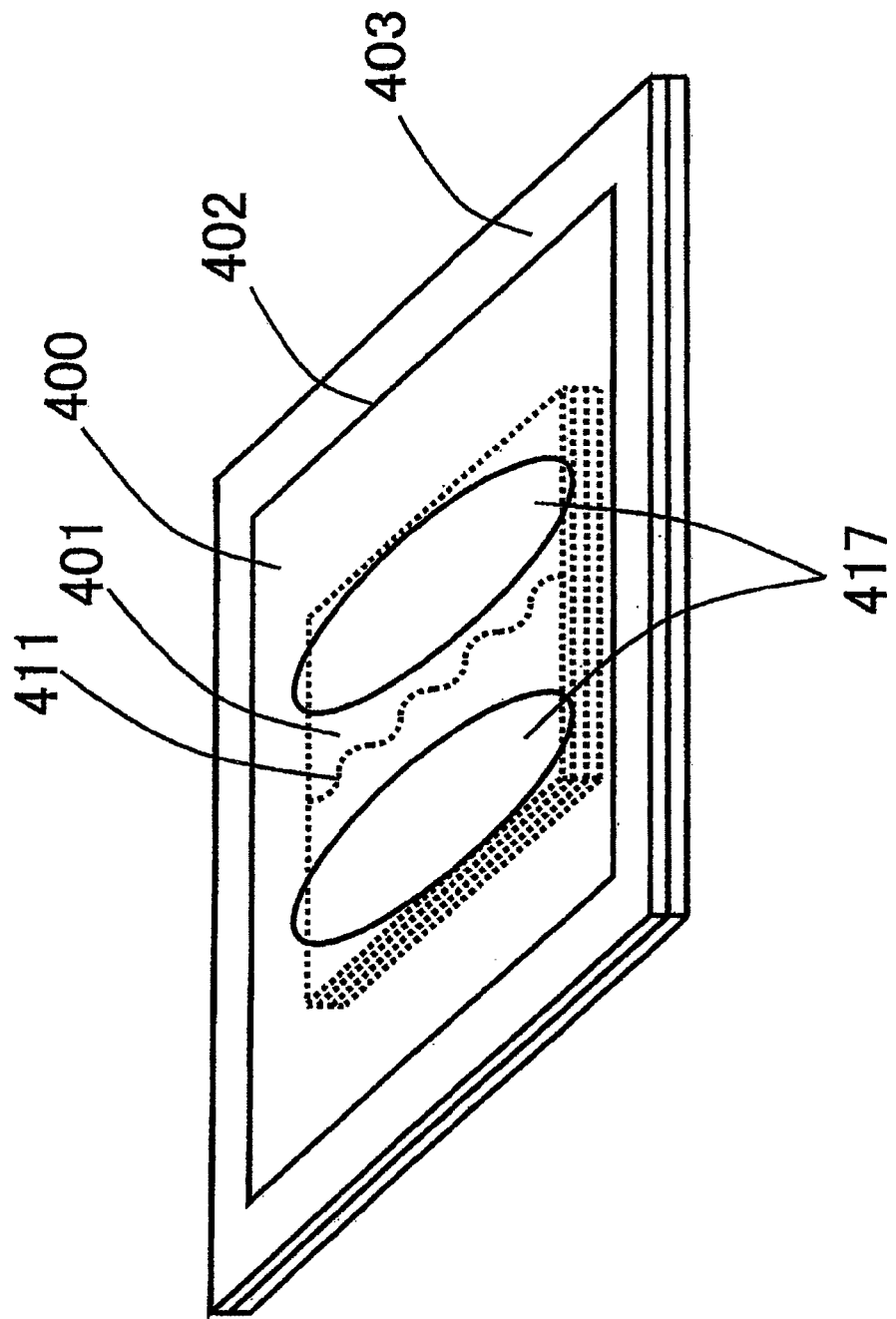
FIG. 4 is a sectional view of another embodiment of the patch package structure of the invention.

In the next place, with reference to FIG. 4, FIG. 4 is a slant view of another embodiment of the patch package structure 400 of the invention. This embodiment has the same constitution as the embodiments shown in FIGS. 1 to 3, unless otherwise indicated. In this embodiment, a patch 401 is disposed in a package 402. A sectional view of this embodiment is shown in FIG. 5.

Figure 5:
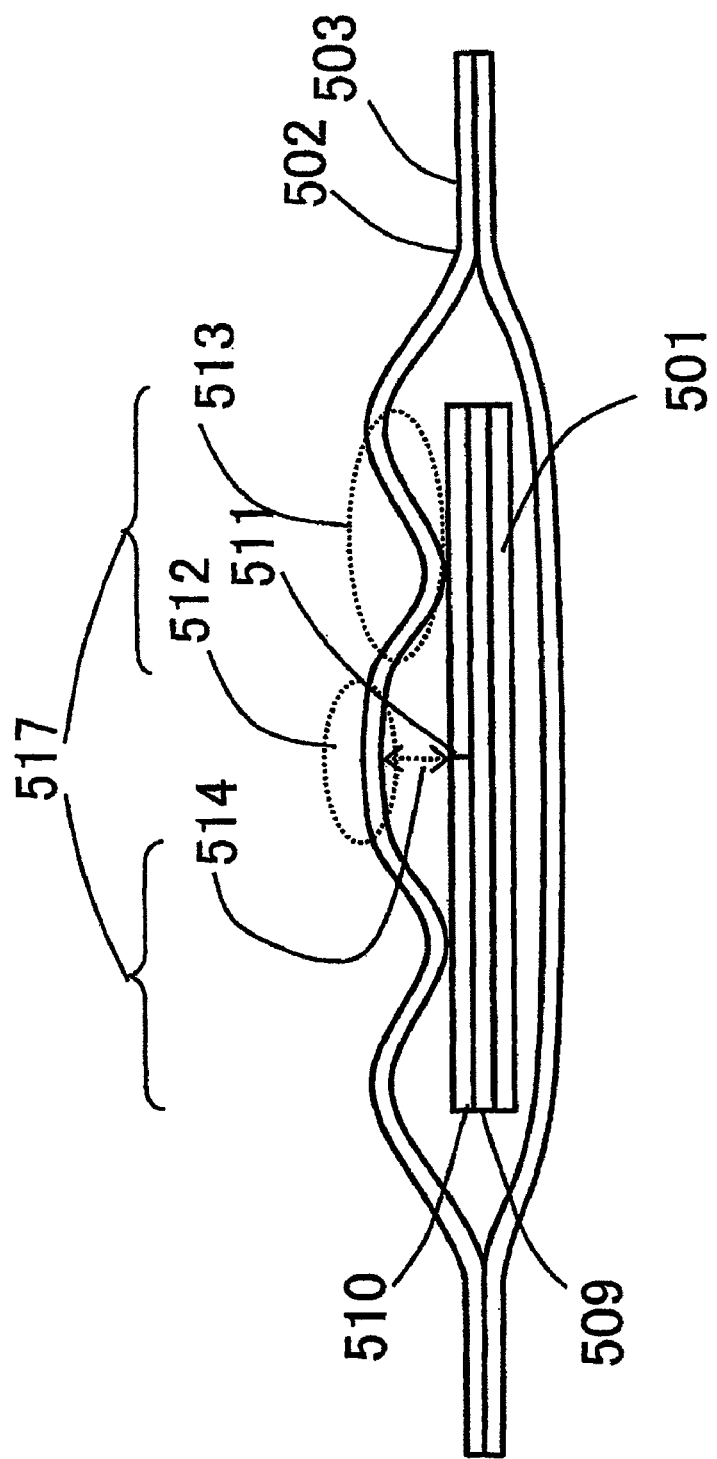
FIG. 5 is a sectional view of still another embodiment of the patch package structure of the invention.

In the embodiment shown in FIG. 5, a patch 501 is disposed in a package 502 in such a manner that a release liner 510 faces the inner surface of a first sheet material 503. The first sheet material 503 has a first region 512 in which the inner surface of the first sheet material 503 faces a cut line 511 formed on a surface of the release liner 510 of the patch 501, and also has a second region 513 in which the inner surface of the first sheet material 503 does not face the cut line 511 on the surface of the release liner 510 of the patch 501. In the second region 513 of the first sheet material 503, a recessed part 517 which is depressed toward the inside of the package is formed.

With reference to FIG. 4 again, the recessed part 417 have a substantially elliptic planar outer shape. The planar outer shape of the recessed part 417 is not particularly limited. Examples thereof include substantially quadrangular shapes, substantially polygonal shapes such as substantially rectangular shapes and substantially triangular shapes, substantially elliptic shapes, substantially circular shapes, and other various shapes. Although the number of recessed part 417 may be either one or more, it is preferably two or more from the standpoint of effectively inhibiting the cut line 411 from coming into contact with the inner surface of the first sheet material 403.

With reference to FIG. 5 again, when the patch 501 is disposed in the package 502, the first sheet material 503 has, in the first region 512, a minimum first distance 514 between the inner surface of the first sheet material 503 and the surface of the release liner 510. In the first region 512, the inner surface of the first sheet material 503 is spaced from the surface of the release liner 510 at the minimum first distance 514.

The first sheet material 503 is molded into such a shape, whereby the cut line 511 on a surface of the release liner 510 is less apt to come into contact with the inner surface of the first sheet material 503. Consequently, even if components of the pressure-sensitive adhesive layer 509 protrude from or flow out through the cut line 511, the components of the pressure-sensitive adhesive layer 509 are effectively inhibited from adhering to the inner surface of the first sheet material 503. Furthermore, as already mentioned above, since an external load is less apt to be imposed on the patch 501 through the first sheet material 503, the protrusion or outflow of the components of the pressure-sensitive adhesive layer 509 from the cut line 511 is effectively inhibited. Incidentally, specific numerical examples showing the size of such a patch package structure are the same as those described above with regard to FIGS. 1 to 3.

In embodiments in which the first sheet material has a recessed part which is depressed toward the inside of the package as in the embodiment shown in FIGS. 4 and 5, since an external load is inhibited from concentrating at the vicinity of the first region, such embodiments are suitable in the case where the first sheet material is formed of a relatively thin or soft material.

Figure 6:
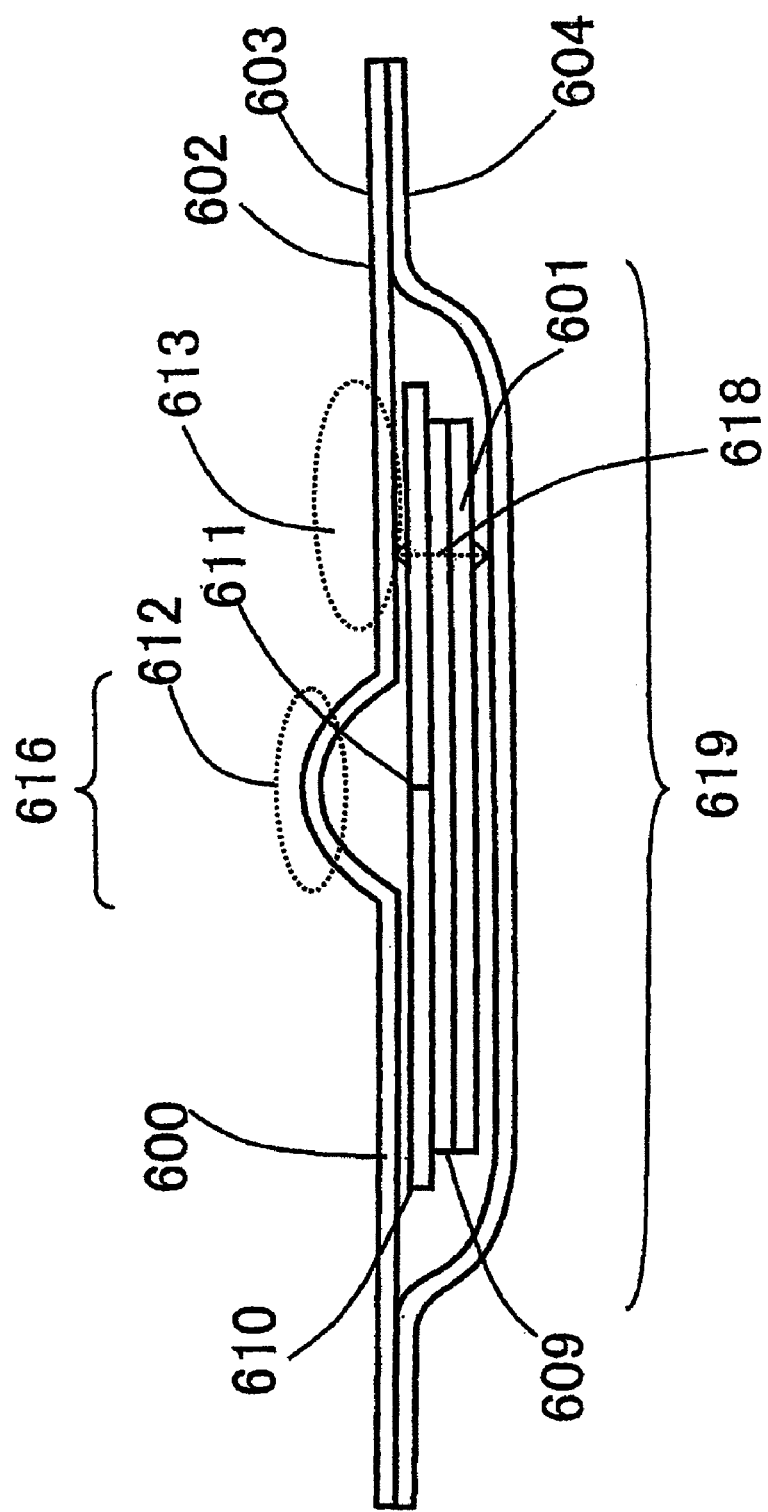
FIG. 6 is a sectional view of a further embodiment of the patch package structure of the invention.

In the next place, with reference to FIG. 6, FIG. 6 is a sectional view of still another embodiment of the patch package structure 600 of the invention. This embodiment has the same constitution as the embodiments shown in FIGS. 1 to 3, unless otherwise indicated. In this embodiment, a patch 601 is disposed in a package 602. In this embodiment, the first sheet material 603 has a first region 612 in which the inner surface of the first sheet material 603 faces a cut line 611 of the release liner 610, and also has a second region 613 in which the inner surface of the first sheet material 603 does not face the cut line 611 of the release liner 610 of the patch 601. In the first region 612 of the first sheet material 603, a first protrudent part 616 which projects toward the outside of the package is formed. The first protrudent part 616 has a planar outer shape which includes a planar outer shape of the cut line 611.

In the embodiment shown in FIG. 6, the first sheet material 603 is substantially planar except for the protrudent part 616. On the other hand, the second sheet material 604 has a planar outer shape which includes the planar outer shape of the patch 601, and also has a second protrudent part 619 projecting toward the outside of the package. The second protrudent part 619 preferably has a height 618 not smaller than the thickness of the patch 601. Owing to the second protrudent part 619, a load is less apt to be imposed on the patch 601 in the thickness direction therefor through the first sheet material 603 or second sheet material 604. Consequently, the protrusion or outflow of components of the pressure-sensitive adhesive layer 609 not only from the cut line 611 but also from the edges of the patch 601 is inhibited.

The embodiment shown in FIG. 6 produces the following effect besides the same effects as those of the embodiments shown in FIGS. 1 to 3. Namely, since the release liner 610 has a planar outer shape including the planar outer shape of the pressure-sensitive adhesive layer 609, and the patch 601 is packed so that the release liner 610 faces the inner surface of the first sheet material 603 of the package 602, even if the components of the pressure-sensitive adhesive layer 609 protrude or flow out from an edge of the patch 601, the components of the pressure-sensitive adhesive layer are effectively inhibited from moving beyond the edge of the release liner 610 to adhere to the inner surface of the first sheet material 603 of the package 602.

Figure 7:
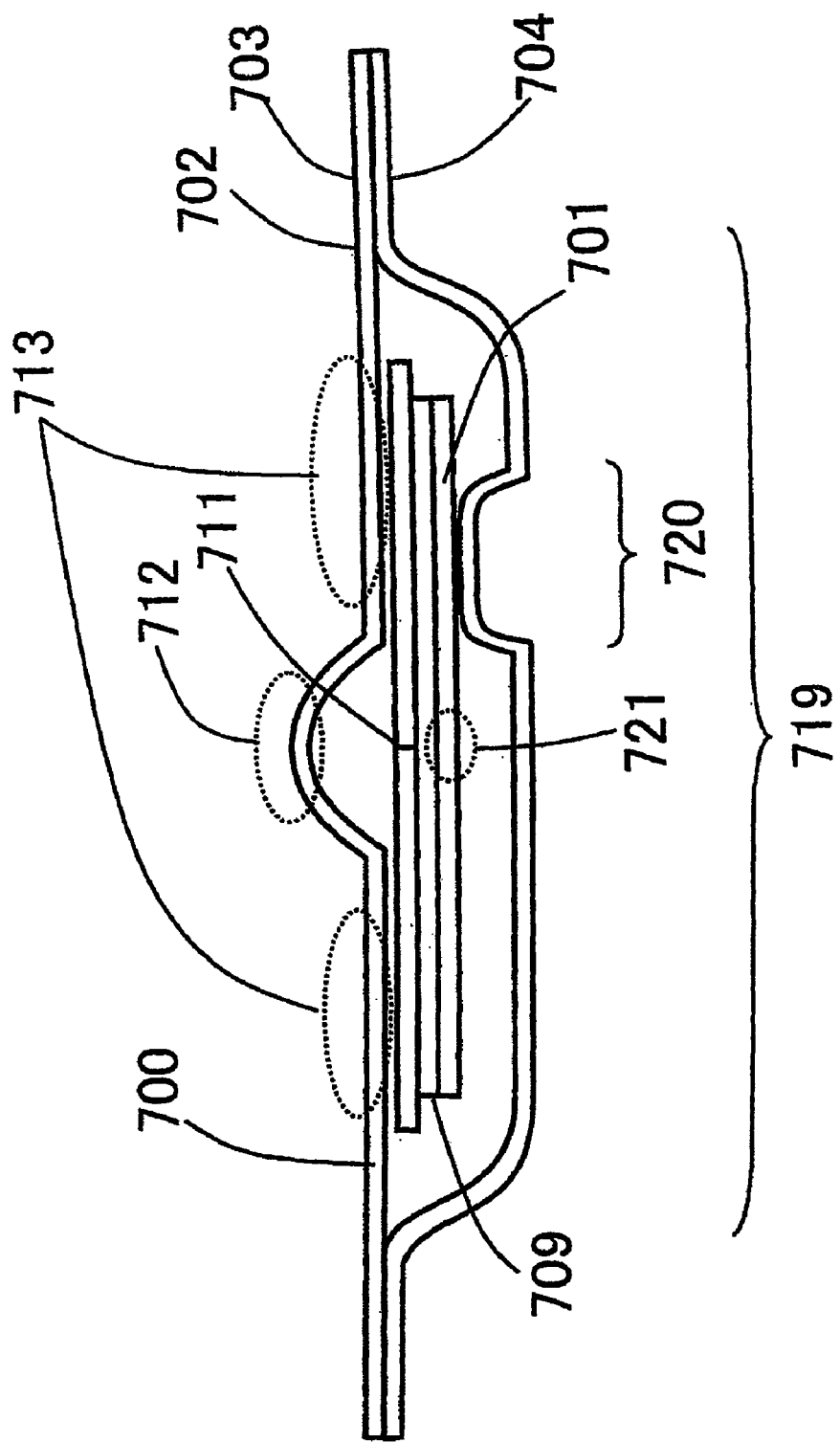
FIG. 7 is a sectional view of still a further embodiment of the patch package structure of the invention.

In the next place, with reference to FIG. 7, FIG. 7 is a sectional view of a further embodiment of the patch package structure 700 of the invention. This embodiment has the same constitution as the embodiment shown in FIG. 6, unless otherwise indicated. In this embodiment, a patch 701 is disposed in a package 702. In this embodiment, the second sheet material 704 is molded so that it has a protrudent part 719 having an upper part and a side part, and the upper part has a recessed part 720 which is depressed toward the inside of the package 702. In this embodiment, the recessed part 720 is formed in such a position that the inner surface of the recessed part 720 does not come into contact with a part 721 of the backing which corresponds to the cut line 711 of the patch 701. Since the second sheet material 704 has such a recessed part 720, an external load is inhibited from concentrating at the vicinity of the cut line. The patch package structure 700 therefore has an effect that components of the pressure-sensitive adhesive layer are effectively inhibited from protruding from or flowing out through the cut line.

In the patch package structure shown as an embodiment in FIG. 7, specific examples of the distance between the inner surface of the first sheet material 703 and the inner surface of the second sheet material 704 in a first region 712 include 1.0-4.0 mm. Specific examples of the distance between the inner surface of the first sheet material 703 and the inner surface of the second sheet material 704 in the second region 713 which corresponds to the recessed part 720 include 0.3-2.0 mm. Specific examples of the distance between the inner surface of the first sheet material 703 and the inner surface of the second sheet material 704 in the second region 713 which does not correspond to the recessed part 720 include 0.5-2.5 mm.

Figure 8:
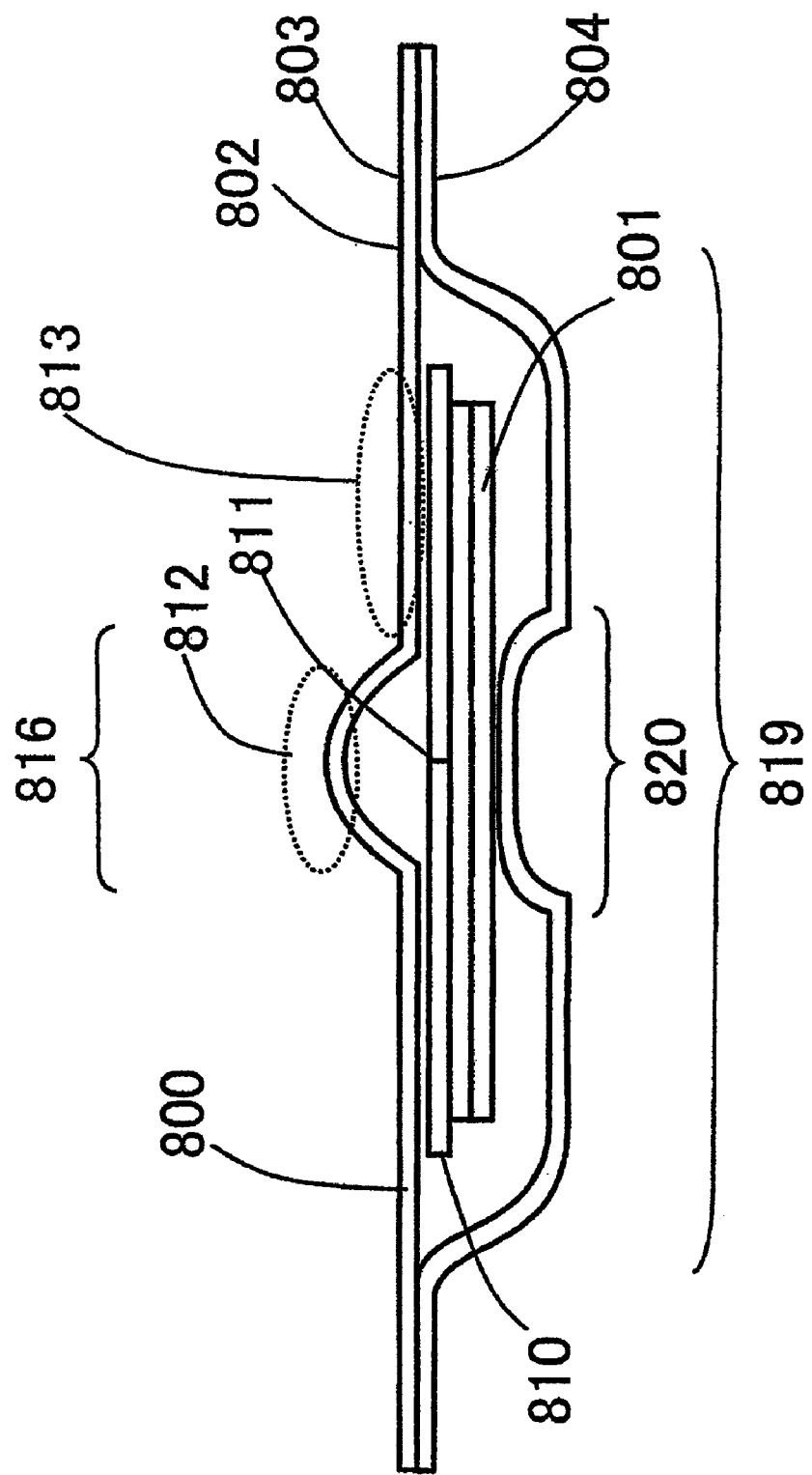
FIG. 8 is a sectional view of still a further embodiment of the patch package structure of the invention.

In the next place, with reference to FIG. 8, FIG. 8 is a sectional view of still a further embodiment of the patch package structure 800 of the invention. This embodiment has the same constitution as the embodiment shown in FIG. 7, unless otherwise indicated. In this embodiment, a patch 801 is disposed in a package 802. The first sheet material 803 has a first region 812 in which the inner surface of the first sheet material 803 faces a cut line 811 of the patch 801, and also has a second region 813 in which the inner surface of the first sheet material 803 does not face the cut line 811 on a surface of the release liner 810 of the patch 801. In the first region 812 of the first sheet material 803, a protrudent part 816 which projects toward the outside of the package is formed. The protrudent part 816 has a planar outer shape which includes a planar outer shape of the cut line 811.

In the embodiment shown in FIG. 8, the second sheet material 804 has a protrudent part 819 having an upper part and a side part, and the upper part has a recessed part 820. In this embodiment, the recessed part 820 of the second sheet material 804 is formed in such a position that when a plane including the patch 801 is defined, then a planar outer shape obtained by projecting the recessed part 820 of the second sheet material 804 on the plane overlaps a planar outer shape obtained by likewise projecting the protrudent part 816 of the first sheet material 803 on the plane. Owing to this constitution, when a plurality of package structures 800 are stacked up in the patch thickness direction in such a manner that the first sheet material 803 of one package structure 800 faces the second sheet material 804 of another package structure 800 and this stack is to be packed into a container such as an inner box, then the protrudent part 816 nearly fits into the recessed part 820. As a result, the package structures 800 can be packed into the container with satisfactory space efficiency. The shape of the recessed part 820 of the second sheet material 804 and the shape of the protrudent part 816 of the first sheet material are not particularly limited. However, from the standpoint of sufficiently producing that effect, it is preferred that the recessed part 820 have a planar outer shape which is the same as the planar outer shape of the protrudent part 816 or includes the planar outer shape of the protrudent part 816. For the same reason, it is preferred that the depth of the recessed part 820 be the same as or larger than the height of the protrudent part 816.

In the patch package structure shown as an embodiment in FIG. 8, specific examples of the distance between the inner surface of the first sheet material 803 and the inner surface of the second sheet material 804 in the first region 812 include 1.0-4.0 mm. Specific examples of the distance between the inner surface of the first sheet material 803 and the inner surface of the second sheet material 804 in the second region 813 include 1.0-4.0 mm.

Figure 9:
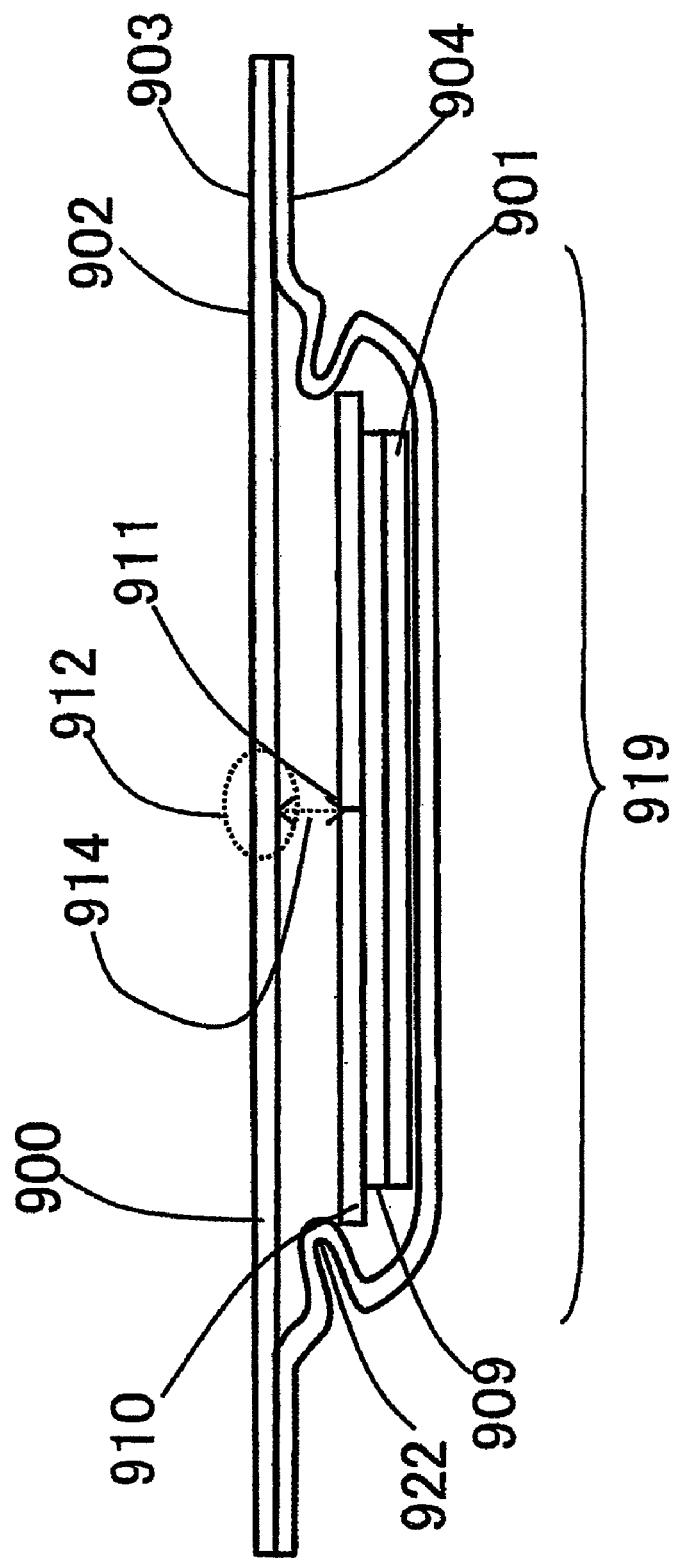
FIG. 9 is a sectional view of still a further embodiment of the patch package structure of the invention.
Figure 10:
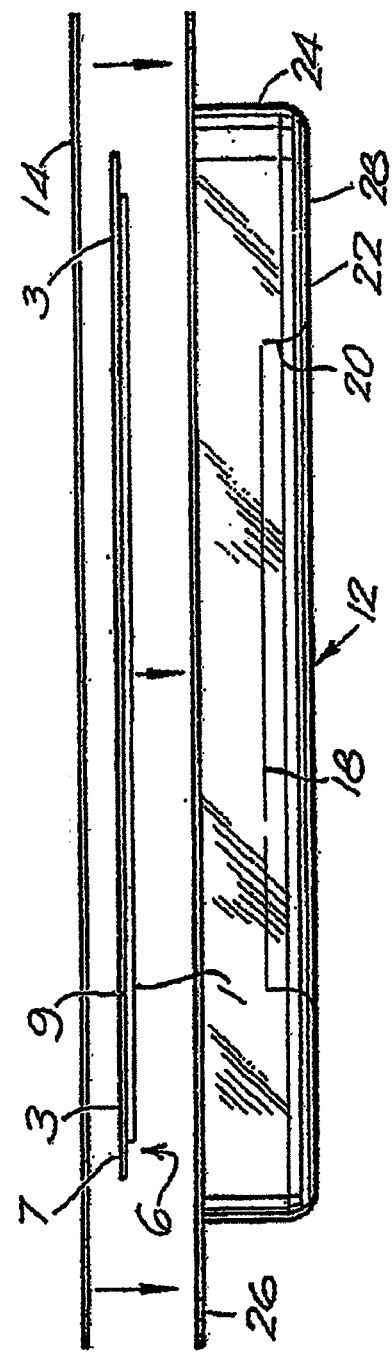
FIG. 10 is a slant view of a conventional patch package structure.

In the next place, with reference to FIG. 9, FIG. 9 is a sectional view of still a further embodiment of the patch package structure 900 of the invention. This embodiment has the same constitution as the embodiment shown in FIGS. 1 and 2, unless otherwise indicated. In this embodiment, a patch 901 is disposed in a package 902. In this embodiment, the patch 901 is disposed in the package 902 formed by sealing a peripheral part of a first sheet material 903 and a peripheral part of a second sheet material 904.

In this embodiment, the first sheet material 903 is an approximately planar sheet which is not especially molded. The first sheet material 903 has a first region 912 in which the inner surface of the first sheet material 903 faces a cut line 911 of the patch 901. In the first region 912, when the patch 901 is disposed in the package 902, the inner surface of the first sheet material 903 and the surface of the release liner 910 of the patch 901 provide a minimum first distance 914 therebetween. In this embodiment, the second sheet material 904 is molded so as to have a protrudent part 919. The protrudent part 919 of the second sheet material 904 has an upper part and a side part, and the side part has a depressed part 922 which is depressed toward the inside of the package 902. The second sheet material 904 is molded so that the patch 901 is supported by the inner surface of the second sheet material 904 at the depressed part 922. The disposition of the depressed part 922 inhibits the sheet-form patch 901 from moving in both the plane directions for the patch 901 and the direction perpendicular thereto. Accordingly, even if components of the pressure-sensitive adhesive layer protrude from or flow out through the cut line 911, the components of the pressure-sensitive adhesive layer are effectively inhibited from adhering to the inner surface of the first sheet material 903.

The first sheet material and second sheet material in the patch package structure of the invention described above are not particularly limited so long as both materials can be sealed together to form the package. Heat-sealable sheet materials are preferred from the standpoint of ease of production. Examples of such packaging materials include films of resins such as polyolefins including polyethylene and polypropylene, polyesters including poly(ethylene terephthalate), and other resins including poly(vinyl chloride) and polyacrylonitrile, metal films such as aluminum foils, materials obtained by vapor-depositing aluminum on these films, and laminated films obtained by laminating two or more thereof.

From the standpoints of impermeability to package contents such as a drug and heat sealability, a polyacrylonitrile film or the like is preferred for use as such a packaging material. From the standpoint of the non-absorptive property of package contents such as a drug, it is preferred to employ a polyester, especially poly(ethylene terephthalate) or the like. From the standpoint of the impermeability to package contents, light rays, or gases, more preferred packaging materials are those resin films which have undergone aluminum vapor deposition and laminated films obtained by laminating an aluminum foil to those resin films. More preferred from the standpoint of combining those properties are laminated films obtained by laminating a polyester, in particular poly(ethylene terephthalate), with a polyacrylonitrile film. Most preferred is a laminated film obtained by laminating a polyester, in particular poly(ethylene terephthalate), with an aluminum foil or vapor-deposited aluminum layer and a polyacrylonitrile film. From the standpoint of the storage stability of package contents such as a drug, a laminated film obtained by laminating a water-impermeable layer and a water-permeable layer respectively to the outer side and inner side of a hygroscopic layer containing a drying agent is also preferred.

Materials and constitutions of the first sheet material and the second sheet material may be the same or different. In the case where one or both of the first sheet material and second sheet material to be used are a molded sheet material, they are preferably made of a rigid material because the molded sheet material is required to retain a given shape. In the case where one or both of these materials are used as an approximately planar unmolded sheet material without being molded, they are preferably made of a flexible material because such unmolded sheet material can be easily sealed with the molded sheet material to thereby facilitate production.

The thickness of the unmolded sheet material is not particularly limited. However, it is preferably 10-200 μm, and more preferably 20-100 μm, from the standpoints of production efficiency and impermeability to ingredients to be packaged in the package structure.

The thickness of the molded sheet material is not particularly limited. It is, however, preferred that the second sheet material have some degree of stiffness because of the necessity of retaining the given shape. From this standpoint, the thickness thereof is preferably 50-300 μm, and more preferably 50-200 μm.

Molding methods for obtaining the molded sheet material having the given shape are not limited. Examples thereof include vacuum/pressure forming, injection molding, and press molding. From the standpoints of suitability for cost reduction, degree of freedom of shapes, material selection, etc., vacuum forming, pressure forming, and the like are preferred.

The patch may be an adhesive preparation in which the pressure-sensitive adhesive layer contains a drug. The drug herein is not particularly limited. Preferred is a drug which can be administered to a mammal such as a human through the skin, i.e., which is percutaneously absorbable. Examples of such drugs include systemic anesthetics, hypnotic agents, antiepileptics, antipyretic/analgesic/antiphlogistic agents, antidizzying agents, psychoneurotics, local anesthetics, skeletal muscle relaxants, agents for autonomous nerve, antispasmodics, anti-Parkinsonian agents, antihistamines, cardiotonics, antiarrhythmics, diuretics, antihypertensives, vasoconstrictors, coronary vasodilators, peripheral vasodilators, antiarteriosclerotic agents, agents for circulatory organs, respiration facilitators, antitussive/expectorant agents, hormone drugs, external-use preparations for purulent diseases, analgesic/antipruritic/astringent/antiphlogistic agents, agents for parasitic skin diseases, hemostats, antipodagrics, agents for diabetes, antineoplastics, antibiotics, chemotherapeutics, narcotics, and smoking renunciation aids.

The content of the percutaneously absorbable drug is not particularly limited so long as it sufficiently produces the effect thereof and does not impair the adhesiveness of the pressure-sensitive adhesive. However, the content thereof in the pressure-sensitive adhesive is, for example, 0.01-70% by weight, preferably 0.1-60% by weight, and more preferably 0.5-40% by weight. In a case where the content thereof is lower than 0.01% by weight, there is a possibility that the remedial effect might be insufficient. In a case where the content thereof is higher than 70% by weight, there is a possibility that skin irritation might occur and such a large drug amount might be economically disadvantageous.

The pressure-sensitive adhesive layer contains a pressure-sensitive adhesive. The pressure-sensitive adhesive is not particularly limited. Examples thereof include acrylic pressure-sensitive adhesives containing an acrylic polymer; rubber pressure-sensitive adhesives such as styrene/diene/styrene block copolymers (e.g., styrene/isoprene/styrene block copolymers and styrene/butadiene/styrene block copolymers), polyisoprene, polyisobutylene, and polybutadiene; silicone pressure-sensitive adhesives such as silicone rubbers, dimethylsiloxane-based polymers, and diphenylsiloxane-based polymers; vinyl ether pressure-sensitive adhesives such as poly(vinyl methyl ether), poly(vinyl ethyl ether), and poly(vinyl isobutyl ether); vinyl ester pressure-sensitive adhesives such as vinyl acetate/ethylene copolymers; and polyester pressure-sensitive adhesives produced from a carboxylic acid ingredient such as dimethyl terephthalate, dimethyl isophthalate, or dimethyl phthalate and a polyhydric alcohol ingredient such as ethylene glycol.

Acrylic pressure-sensitive adhesives or rubber pressure-sensitive adhesives are preferred among such pressure-sensitive adhesives because acrylic or rubber pressure-sensitive adhesives give a pressure-sensitive adhesive layer which is capable of holding a liquid component therein and hence can give a soft feeling during wear on the skin. In particular, acrylic pressure-sensitive adhesives are preferred because they can be easily crosslinked and give a pressure-sensitive adhesive layer capable of holding a large amount of a liquid component therein.

Examples of the acrylic pressure-sensitive adhesives include acrylic ester pressure-sensitive adhesives containing as the main component a polymer comprising monomer units derived from one or more $C_{2-18}$ alkyl esters of (meth)acrylic acid. Examples of the rubber pressure-sensitive adhesives include those containing as the main component at least one member selected from polyisobutylene, polyisoprene, and styrene/diene/styrene copolymers.

The liquid component is not particularly limited. From the standpoint of compatibility with the pressure-sensitive adhesive layer, organic liquid components are prepared. Although the organic liquid components are not particularly limited, those having the effect of accelerating percutaneous absorption are preferred. Examples of such organic liquid ingredients include glycols such as ethylene glycol, diethylene glycol, propylene glycol, triethylene glycol, polyethylene glycol, and polypropylene glycol; fats and oils such as olive oil, caster oil, squalane, and lanolin; hydrocarbons such as liquid paraffin; various surfactants; ethoxy stearyl alcohol; glycerol monoesters such as oleic acid monoglyceride, caprylic acid monoglyceride, and lauric acid monoglyceride, glycerol diesters, glycerol triesters, and mixtures thereof; alkyl esters of fatty acids, such as ethyl laurate, isopropyl myristate, isotridecyl myristate, octyl palmitate, isopropyl palmitate, ethyl oleate, and diisopropyl adipate; higher fatty acids such as oleic acid and caprylic acid; and other compounds including N-methylpyrrolidone and 1,3-butanediol.

In the case where a liquid component is contained in the pressure-sensitive adhesive layer, there is a possibility that during storage of the patch, components of the pressure-sensitive adhesive layer might protrude from or flow out through the cut line formed in the release liner. The invention is advantageously practiced especially in such a case. From this standpoint, the content of the liquid component in the pressure-sensitive adhesive layer is preferably 5-70% by weight, more preferably 10-65% by weight, and most preferably 15-60% by weight.

When the pressure-sensitive adhesive layer is relatively thick, the protrusion or outflow of components of the pressure-sensitive adhesive layer from the cut line is likely to occur. The invention is advantageously practiced especially in such a case. From this standpoint, the thickness of this pressure-sensitive adhesive layer is preferably 20-300 μm, more preferably 30-250 μm, and most preferably 50-200 μm.

The explanations of the invention are merely illustrative, and modified embodiments thereof which do not depart from the spirit of the invention are hence intended to be within the scope of the invention. Such modified embodiments should not be construed ad departing from the spirit and scope of the invention.

This application is based on Japanese patent application No. 2007-175809 filed Jul. 4, 2007, the entire contents thereof being hereby incorporated by reference.

Further, all references cited herein are incorporated in their entireties.

What is claimed is:

1. A patch package structure which comprises:
    a package comprising a first sheet material and a second sheet material, said first and second sheet materials being sealed together in peripheral parts thereof; and
    a patch disposed in the package,
    wherein the patch comprises a backing, a pressure-sensitive adhesive layer laminated on at least one side of the backing, and a release liner which protects a pressure-sensitive adhesive surface of the pressure-sensitive adhesive layer, said release liner having an external surface, wherein said external surface has a cut line supporting a peel-off of the release liner at the time of using the patch, wherein the patch is disposed in the package so that the release liner faces the inner surface of the first sheet material, wherein the first sheet material has a first region in which the inner surface of the first sheet material faces the cut line of the release liner, and the first sheet material has in the first region a minimum first distance between the inner surface of the first sheet material and the external surface of the release liner, and wherein the first sheet material has in the first region a protrudent part which projects toward an outside of the package, said protrudent part having an outer shape which includes an outer shape of the cut line.

2. The patch package structure according to claim 1, wherein the first sheet material has a second region in which the inner surface of the first sheet material does not face the cut line of the release liner, and the first sheet material has in the second region a recessed part which is depressed toward the inside of the package.

3. The patch package structure according to claim 1, wherein the second sheet material has a protrudent part which protrudes toward the outside of the package, said protrudent part having an outer shape which includes an outer shape of the patch.

4. The patch package structure according to claim 3, wherein the protrudent part of the second sheet material has a side part and an upper part, and the upper part has a recessed part which is depressed toward the inside of the package, said recessed part being disposed at such a position that the inner surface of the package at the recessed part does not come into contact with a part of the backing which corresponds to the cut line of the release liner of the patch.

5. The patch package structure according to claim 3, wherein the protrudent part of the second sheet material has a side part and an upper part, and the side part has a depressed part which is depressed toward the inside of the package, said patch being supported by the inner surface of the second sheet material at the depressed part.

6. The patch package structure according to any one of claims 1 or 2 to 5, wherein the pressure-sensitive adhesive layer of the patch contains a liquid component.

7. The patch package structure according to claim 1, wherein the patch is an adhesive preparation comprising a pressure-sensitive adhesive layer containing a drug.

* * * * *